United States Patent [19]

Mintz

[11] Patent Number: 5,349,100
[45] Date of Patent: Sep. 20, 1994

[54] CHIRAL METALLOCENE COMPOUNDS AND PREPARATION THEREOF BY CREATION OF A CHIRAL CENTER BY ENANTIOSELECTIVE HYDRIDE TRANSFER

[75] Inventor: Eric A. Mintz, Dorravile, Ga.

[73] Assignee: Exxon Chemical Patents Inc., Linden, N.J.

[21] Appl. No.: 636,598

[22] Filed: Jan. 2, 1991

[51] Int. Cl.$^5$ .................. C07C 13/00; C07C 2/02
[52] U.S. Cl. ...................... 585/350; 585/375; 556/43; 556/47; 556/53; 556/60; 556/143
[58] Field of Search ............ 585/350, 375; 556/43, 556/47, 53, 60, 143

[56] References Cited

PUBLICATIONS

Morrison et al., *Organic Chemistry*, 3rd Ed., Allyn and Bacon Inc., Boston, pp. 123–125 (1973).

Daniel T. Mallin et al., "Synthetic, X-ray structural and polymerization studies on isopropyltetramethylcyclopentadienyl derivatives of titanium", *J. Organomet Chem.*, vol. 381, 1990, pp. 35–44.

Jerome C. Pando, Eric Mintz, "5-Methoxy-2,3,4,5-tetramethylcyclopent-2-enone, a Synthetic Equivalent For 2,3,4,5-Tetramethylcyclopentadienone: Application to the Synthesis of 1,2,3,4-Tetramethylfulvene", *Tetrahedron Letters*, vol. 30, No. 36, 1989, pp. 4811–1812.

Gerhard Erker et al., "Double Stereodifferentiation in the Formation of Isotactic Polypropylene at Chiral (C$_5$H$_4$CHMePh)$_2$ZrCl$_2$/Methylalumoxane Catalysts", *Angew. Chem. Int. Engl.* 28, 1989 No. 5, pp. 628–629.

Dennis M. Bensley, Jr. and Eric A. Mintz, "1,2,3,4,6-Pentamethylfulvene: a convenient precursor to substituted tetramethylcyclopentadienyl transition metal complexes" *J. Organomet. Chem.*, vol. 353, 1988, pp. 93–103.

Dennis M. Bensely, Jr. et al. "Synthesis of [C$_5$(CH$_3$)$_4$H]CH$_2$CH$_2$CH$_2$P(C$_6$H$_5$)$_2$: A Novel Heterodifunctional Ligand Possessing Both a Tetramethylcyclopentadiene and a Remote Diphenylphosphine Functionality". *J. Org. Chem.*, vol. 53, 1988, p. 4417.

Ronald L. Halterman and K. Peter C. Hollhardt, "Synthesis and Asymmetric Reactivity of Enantiomerically Pure Cyclopentadienyl metal Complexes Derived from the Chiral Pool", *Organometallics*, 1988, vol. 7, pp. 883–892.

Emilio E. Bunel et al., "Synthesis of p–Phenylene– and p–Biphenylene–Bridged Methylated Bionuclear Ferrocenes" *Organometallics*, vol. 7 No. 2, 1988, pp. 474–476.

George W. Parshall, William A. Nugent, "Making pharmaceuticals via homogeneous catalysis", *Chemtech*, Mar. 1988, pp. 184–190.

George W. Parshall and William A. Nugent, "Functional chemicals via homogeneous catalysts", *Chemtech*, May 1988, pp. 314–320.

George W. Parshall, William A. Nugent, "Homogeneous catalysis for agrochemicals, flavors, and fragrances", *Chemtech*, Jun. 1988, pp. 376–383.

Paavoó O$_5$. Lumme and Urho Turpeinen, "Crystal and molecular structure of [3-($^5$n–tetramethylcyclopentadienyl)-1-(n$^6$–meisityl)propane]ieridium(II) bistetrafluoroborate mononitromethane", *J. Organomet. Chem.*, vol. 348, 1988, pp. 255–260.

Gallucci, et al. "Bis(isodicyclopentadienyl) Complexes of the Goup 4 Transition Metals. Stereoselective Syn-
(List continued on next page.)

*Primary Examiner*—José G. Dees
*Assistant Examiner*—Porfirio Nazario
*Attorney, Agent, or Firm*—M. Susan Spiering; Catherine L. Bell

[57] ABSTRACT

There are provided enantiomerically enhanced chiral substituted cyclopentadienyl ligands, and compounds thereof, and a process for their making comprising contacting an optionally substituted fulvene having a prochiral carbon 6 with a lithium salt of an amine, amino acid or amide to effectuate enantioselective hydride addition to the carbon 6 of the fulvene so as to create a chiral center. There are further provided enantiomerically enhanced chiral organometallic complexes having one or more chiral substituted cyclopentadienyl groups.

17 Claims, No Drawings

PUBLICATIONS thesis and Crystal Structures of the Titanocene and Zirconocene Dichloride Derivatives" *Organometallics,* vol. 6, 1987, pp. 15–19.

J. F. Buzinkai and R. R. Schrock, "Heterobimetallic Complexes Connected by Peralkylated Cyclopentadienyl Rings" *Organometallics,* vol. 6, 1987, pp. 1447–1452.

Ronald L. Halterman et al., "A designed, Enantiomerically Pure, Fused Cyclopentadienyl Ligand with $C_2$ Symmetry: Synthesis and Use in Enantioselective Titanocene–Catalyzed Hydrogenations of Alkenes", *J. Am. Chem. Soc.,* vol. 109, 1987, pp. 8105–8107.

N. E. Schore and B. E. LaBelle, "Reactions of [(Diphenylphosphino)methyl]lithium with Dimethylfulvene", *J. Org. Chem.,* vol. 46, 1987, pp. 2306–2310.

H. M. R. Heffmann and Oskar Koch, "Regioselective Preparation of Vinylcyclopentadienes and Selected Cycloaditions", *J. Oreg. Chem,* vol. 51, 1986, pp. 2939–2944.

Leo A., Paquette, et al., "$\pi$–Facial Stereoselectivity Operational during Conversion of Isodicyclopentadienes to Metallocene Derivatives", *Organometallics,* vol. 5, 1986, pp. 490–499.

Lihong Shen and Eric A. Minz, "Novel Reduction of 6-t Butylfulvene by Diethylaminolithium and 1,2,3,4-Tetrahydroisoquinolinyllithium" submitted to Tetrahedron Letters, Jan. 1981.

Jerome C. Pando, et al., "5–Methyoxy-and 5-Phenoxy-2,3,4,5-Tetramethylcyclopent-2-Enone as Synthetic Equivalents for 2,3,4,5-Tetramethylcyclopentadienone; Synthesis of 1,2,3,4-Tetramethylfulvene and 1,2,3,4,6-Pentamethylfulvene", Tetrahedron Letters, vol. 30, 1989.

H. B. Kagan, "Chiral Ligands in Asymmetric Catalysis By Transition Metal Complexes", *Annals New York Academy of Sciences,* 1980, pp. 1–15.

Jack Hine and David B. Knight, "Base-Catalyzed Deuterium Exchange of 6,6-Dimethylfulvene" *J. Org. Chem,* vol. 45, 1980, pp. 991–998.

William F. Little and Robert C. Koestler, "Preparation of Substituted Ferrocenes from Fulvenoid Compounds", *J. Org. Chem.,* vol. 26, Sep. 1961, pp. 3245–3247.

David B. Knight, et al., "Protonation and Deuteration of the Isopropenylcyclopentadienyl Anion. Trapping of the Isomeric Product Mixture", *J. Org. Chem.,* vol. 37, No. 5, 1972, pp. 688–692.

Jack Hine and David B. Knight, "Protonation of the Isopropenylcyclopentadienyl Anion", *J. Org. Chem.,* vol. 35, No. 11, 1970, pp. 3946–3949.

Carol M. Fendrick, et al. *Organometallics,* vol. 3, 1983, pp. 819–812.

S. Couturier and B. Gautheron, "Synthesis and Reactions of Substituted Zirconocene and Hafnocene Dimethyls and the Corresponding Dihydrides", *J. Organomet. Chem.,* vol. 157, 1978, pp. C61–C63.

P. Renault, et al., "Chlorures De Mono-et Dialkyl-Zirconocene et–Hafnocene", *J. Organomet. Chem.,* vol. 148, 1978, pp. 35–42.

J. C. LeBlanc and C. Moise, "Complexes Derives Du Dichlorure De Titanocene A Pseudoasymetrie Centrometallee", *J. Organomet. Chem.,* vol. 131, 1977, pp. 35–42.

S. Couturier et al., "Synthese Et Reactivite de Nouveaux Dihydrurozirconocenes et Hafnocenes substitues Achiraux et Chiraux", *J. Organomet. Chem.,* vol. 195, 1980, pp. 291–306.

Franz Wochner, et al., "Syntheses and Crystal Structures of Ethylene–Bridged Titanocene and Zirconocene Derivatives with Permethylated Ring Ligands", *J. Organomet. Chem.,* vol. 288, 1985, pp. 69–77.

Richard S. Threlkel and John E. Bercaw, "A convenient Synthesis of alkyltetramethylcyclopentadienes and Phenyltetramethylcyclopentadiene", *J. Organomet. Chem.,* vol. 136, 1977, pp. 1–5.

H. J. Scholz and H. Werner, "Synthese Von $Li_2[C_5Me_4)_2CH_2]$Und Ringverbruckter Rhodiium–Zeikernkomplexe Mit Dem $(C_5Me_4)_2CH_2$–Dianion Als Burckenliganden", *J. Org. Chem.,* vol. 303, 1986, pp. C–8–C12.

David Feitler and George M. Whitesides, "Convenient Preparations of 1,2,3,4,5-Pentamethylcyclopentadiene and 1-Ethyl-2,3,4,5-tetramethylcyclopentadiene", *Inorg. Chem.,* vol. 15, No. 2, 1976, pp. 466–469.

Donald J. Cram and Donalr R. Wilson, "Studies in Stereochemistry. XXXIII. Approaches to Models for 1,3-ASymmetric Induction", *J. Am. Chem. Soc.,* vol. 85, May 5, 1963, pp. 1249–1257.

Gilbert M. Brown and Norman Sutin, "A Comparison of the Rates of Electron Exchange Reactions of Ammine Complexes of Ruthenium (II) and–(III) with the Predictions of Adiabatic, Outer-Sphere Electron (List continued on next page.)

PUBLICATIONS

Transfer Models", JACS, vol. 101, No. 4, pp. 883–895 (1979).

William S. Knowled, "Asymmetric Hydrogenation", *Acc. Chem. Res.*, vol. 15, 1983, pp. 106–112.

Charles P. Casey, et al., "Synthesis of Molybdenum-Rhodium and Molybdenum-Iridium Compounds Linked by a Heterodifunctional Ligand and Formation of Molybdenum-Iridium Dihydrides by Reaction with Molecular Hydrogen", *J. Am. Chem. Soc.*, vol. 105, 1983, pp. 7574–7580.

M. F. Semmelhack et al., "Reduction of Coordinated Carbon Monoxide to 'Zirconoxy' Carbenes with Permethylzirconocene Dihydride", *J. Am. Chem. Soc.*, vol. 101:1, Jan. 3, 1979, pp. 218–220.

Josephine Paw Blaha and Mark S. Wrighton, "Relative Importance of Dissociative Loss of Carbon Monoxide and Formation of Benzyl Radicals from Photoexcitation of $(n^5-C_5R_5)Fe(CO)_2(^1n-CH_2C_6H_5)$ and Evidence for Reaction of Carbon Monoxide with 17-Electron Radicals", *J. Am. Chem. Soc.*, vol. 107, 1985, pp. 2694–2702.

Donald J. Harvan, et al., "Synthesis of $(C_6H_5)_2PCH_2Si(CH_3)_2C_5H_4Li$: A Novel Heterodifunctional System for the Directed Linkage of Dissimilar Transition Metal Fragments", *J. Am. Chem. Soc.*, vol. 101:24, Nov. 21, 1979, pp. 7410–7412.

Juan M. Manriquez, et al., "Reduction of Carbon Monoxide Promoted by Alkyl and Hydride Derivatives of Permethylzirconocene", *J. Am. Chem. Soc.*, vol. 100:9, Apr. 26, 1978, pp. 2716–2724.

C. F. H. Allen and J. A. VanAllan, "Dimerization of Cyclopentadienones", *J. Am. Chem. Soc.*, vol. 72, Nov. 1950, pp. 5165–,5167.

Peter T. Wolczanski and John E. Bercaw, "On the Mechanisms of Carbon Monoxide Reduction with Zirconium Hydrides", *Acc. Chem. Res.*, vol. 13, 1980, pp. 121–127.

Prof. Dr. K. Hafner, et al., "Fulvenes as Isomers of Benzenoid Compounds", *Angew. Chem. internat. Edit.* vol. 2, 1963, No. 3, pp. 123–134.

Ernst D. Bergmann, "Fulvenes and Substituted Fulvenes", Institute for Advanced Study, Princeton, New Jersey, Apr. 12, 1967, pp. 41–75.

CHIRAL METALLOCENE COMPOUNDS AND PREPARATION THEREOF BY CREATION OF A CHIRAL CENTER BY ENANTIOSELECTIVE HYDRIDE TRANSFER

BACKGROUND OF THE INVENTION

1. Field of the Invention

This invention relates to enantiomeric chiral compounds and a process for their stereoselective preparation. In another aspect this invention relates to enantiomerically enhanced or pure chiral cyclopentadiene ligands and compounds and a stereoselective process for their making by the creation of a chiral center at the carbon 6 position of a prochiral fulvene compound by hydride transfer. In yet another aspect, this invention relates to enantiomeric chiral Group III B - VIII B (the chemical Groups herein are as referenced to the Periodic Table of Elements, *CRC Handbook of Chemistry and Physics*, 68th ed. 1987-1988) organometallic complexes and a process for their stereoselective preparation.

2. Description of the Prior Art

Stereochemistry refers to the three-dimensional spatial configurations of molecules. Stereoisomers are compounds which have identical chemical constitution, but differ as to the orientation of the atoms or groups in three dimensional space. Stereoisomers fall into one of two broad classes: optical isomers and geometric (cis-trans) isomers. Enantiomers are one type of optically active three-dimensional isomers that are mirror image structures, which form as the result of the presence of one or more asymmetric or chiral centers. These mirror image forms compare to each other structurally as do the right and left hands when the chiral carbon atoms, C*, are lined up. For example, in the enantiomeric forms of glyceraldehyde, the two structures are mirror images of each other and cannot be made to coincide:

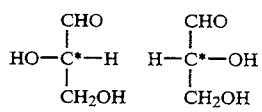

There are several different nomenclature used in to refer to enantiomers: R/S; +/−; and d/l.

Pairs of stereoisomers differ so little in structure, and hence in physical properties, that they are generally differentiated by the use of a polarimeter, which measures the amount of rotation the compound imparts to polarized light as it passes through the compound. Yet despite the close similarity, one isomer of a pair may serve as a nourishing food, or as an antibiotic, or as a powerful heart stimulant, and the other isomer may be useless or even harmful. One of the most difficult problems in the preparation of compounds is the control of stereochemistry, and in particular the preparation of enantiomerically pure compounds. One of the most dramatic examples of the importance of chirality control was the use of the drug thalidomide, which was manufactured and sold as a racemic mixture (mixture4of the optical isomers wherein the mixture is optically inactive). One optical isomer produced the desired therapeutic effect, while the enantiomer, which was assumed to be pharmacologically inert, led to fetal deformities.

Chiral catalytic complexes could be utilized to facilitate enantioselective transformations. For example the enantioselective hydrogenation of acetamidocinnamic acid is catalyzed by the presence of a chiral rhodium catalyst. Transition metal organometallic complexes have long been used to catalyze chemical reactions. Recently transition metal complexes incorporating chiral chelating diphosphine ligands have been successfully utilized to effect enantioselective hydrogenations. However, the stereo-differentiating ability of these complexes can suffer due to the lability of phosphine ligands.

The tremendous potential of utilizing chiral organometallic complexes to carry out enantioselective transformations is hindered by the lack of readily available enantiomerically enhanced (that is, an excess of one of the enantiomers) or pure organometallic complexes, and enantiomerically enhanced or pure ligands or compounds from which to make enantiomerically enhanced or pure organometallic complexes.

Chiral cyclopentadienes are considered to be a suitable starting point for making enantiomeric organometallic complexes, however, only a small number of chiral cyclopentadienes are known and only a few of them are enantiomerically enhanced or pure. Generally, synthesis of chiral compounds from achiral reactants typically will yield the racemic modification or mixture. The enantiomers must then be separated (resolved) by special methods that are very difficult and yield less than desired results. A method that would produce an excess of the desired enanthomer could rely less on resolution techniques than a process that produced a racemic or essentially racemic mixture. There have been other attempts to develop enantiomerically enhanced or pure cyclopentadienyl ligands or compounds that have focused on preparing chiral cyclopentadienyl ligands from inexpensive naturally occurring enantiomerically enhanced or pure compounds. Unfortunately many of these routes require several synthetic steps to transform a naturally occurring starting material into a cyclopentadienyl derivative.

The addition of nucleophiles to fulvenes has proven to be a successful route for the preparation of substituted cyclopentadienyl ligands. Generally, a fulvene of the following general formula that is disubstituted at the 6 position:

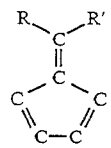

is reacted with a nucleophile R" selected from H, $CH_3$ and $C_6H_5$, $CH_2P(C_6H_5)_2$, to yield the following substituted cyclopentadienyl ligand:

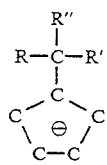

wherein R is selected from $CH_3$ and $C_6H_5$, and R' is selected from H, $CH_3$ and $C_6H_5$. While the carbon 6 may potentially be a chiral center, the cyclopentadienyl ligand product will be a racemic modification or mixture. Furthermore, the scope of this reaction has been generally limited because the reaction of fulvene derivatives with heteroatom based nucleophiles has been found to lead to deprotonation rather than nucleophilic addition.

Therefore, the need exists in the art for an efficient, simple process for producing from fulvene compounds di-substituted at the 6 position, enantiomerically enhanced or pure cyclopentadienyl derivatives which could then be made into enantiomerically enhanced or pure organometallic compounds, without an undue amount of synthetic steps, and without having to rely entirely on resolution techniques.

SUMMARY OF THE INVENTION

According to one embodiment of this invention there are provided enantiomerically enhanced chiral optionally substituted cyclopentadienyl ligands and compounds thereof of the following general formula III:

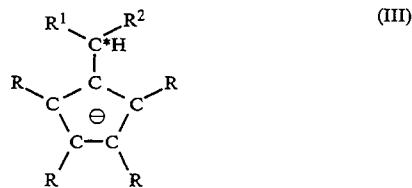

(III)

wherein C* is a chiral carbon center meaning that each group appended to C* is different; each R is independently H, a $C_1$ or higher desirably $C_1$-$C_{12}$ and more desirably $C_1$-$C_8$, substituted or unsubstituted, aliphatic, cyclic or two neighboring R groups can be joined together to form one or more rings of 5 or more carbon atoms, preferably 5 to 8 carbon atoms and desirably 6 carbon atoms; $R^1$ and $R^2$ cannot be the same and each is independently selected from a $C_1$ or higher, substituted or unsubstituted, aliphatic, cyclic or heterocyclic hydrocarbon radical.

According to another embodiment of this invention there is provided a stereoselective process of preparing enantiomerically enhanced chiral optionally substituted cyclopentadienyl ligands and compounds thereof of the above general formula III comprising contacting an optionally substituted fulvene having a prochiral carbon at the carbon 6 position of general formula I:

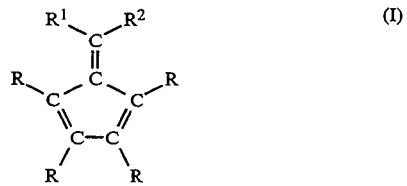

(I)

with a lithium salt of a chiral amide, chiral amino acid, or a primary or secondary chiral amine in a suitable solvent and under suitable reaction conditions so as to effectuate an enantioselective hydride transfer, wherein R, $R^1$ and $R^2$ are as defined above.

According to still another embodiment of this invention there are provided enantiomerically enhanced or pure chiral organometallic complexes having one or more chiral substituted cyclopentadienyl groups.

DETAILED DESCRIPTION OF THE INVENTION

The substituted fulvene compounds or derivatives thereof that are useful in the present invention, are fulvenes di-substituted at the carbon 6 position with optional substitution on the cyclopentadiene ring and are of the general formula I:

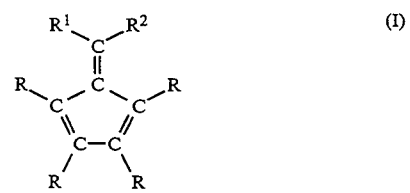

(I)

wherein the carbon 6 is a prochiral carbon center meaning that it currently has three different groups attached to it, and the addition of a fourth different group will create a chiral center; each R is independently H or a $C_1$ or higher, substituted or unsubstituted, aliphatic, cyclic or heterocyclic hydrocarbon radical or two neighboring R groups can be joined together to form one or more rings of 5 or more carbon atoms preferably 5 to 8 carbon atoms and desirably 6 carbon atoms; $R^1$ and $R^2$ cannot be the same and each is independently selected from a $C_1$ or higher, substituted or unsubstituted, aliphatic, cyclic or heterocyclic hydrocarbon radical. Preferably, each R is independently H or a $C_1$-$C_8$ alkyl radical, or a substituted or unsubstituted aromatic radical, and $R^1$ and $R^2$ cannot be the same and each is independently selected from $C_1$-$C_8$ alkyl radical, or a substituted or unsubstituted aromatic radical. Examples of suitable fulvenes include 6-alkyl-6-arylfulvene. Most preferably, each R is H or a $C_1$ to $C_3$ alkyl radical, and each $R^1$ and $R^2$ cannot be the same and each is independently selected from $C_1$ to $C^3$ alkyl radicals and phenyl radicals. Exemplary fulvene compounds useful in the present invention include those of the general group 6-methyl-6-phenylfulvene, 6-methyl-6-ethylfulvene, 6-methyl-6-propylfulvene, 6-ethyl-6-propylfulvene, 6-ethyl-6-phenylfulvene, 6-propyl-6-phenylfulvene.

The lithium salts of chiral amides, chiral amino acids, and primary and secondary chiral amines useful in the present invention are those in which a hydrogen is on a carbon alpha to the nitrogen. Suitable lithium salts of amines include lithium salts of chiral primary and secondary cyclic, acyclic, heterocyclic, open chain and functionalized amines. Suitable lithium salts of amides include lithium salts of chiral cyclic, acyclic, and heterocyclic amides. Lithium salts of chiral amino acids are also suitable for use in the present invention. Exemplary lithium salts useful in the present invention include the lithium salt of 2-methylindoline, dilithium salt of (S)-(−)-2-pyrrolidone-5-carboxylic acid, and the dilithium salt of L proline.

Preferably, the lithium salt will be enantiomerically enhanced or pure to effectuate an enantioselective hydride transfer.

The enantiomerically enhanced chiral optionally substituted cyclopentadienyl ligands of the present invention are of the following general formula III:

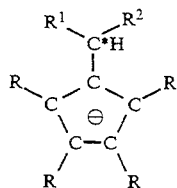

(III)

wherein C* is a chiral carbon center meaning that each group appended to C* is different; each R is independently H or a $C_1$–$C_8$, substituted or unsubstituted, aliphatic or cyclic, hydrocarbon radical or two neighboring R groups can be joined together to form one or more rings of 5 or more carbon atoms, preferably 5 to 8 carbon atoms and desirably 6 carbon atoms; $R^1$ and $R^2$ cannot be the same and each is independently selected from a $C_1$–$C_8$, substituted or unsubstituted, aliphatic, cyclic or heterocyclic, hydrocarbon radicals. Preferably, each R is independently H or a $C_1$ or higher alkyl radical, or a substituted or unsubstituted aromatic radical, and $R^1$ and $R^2$ cannot be the same and each is independently selected from $C_1$ or higher alkyl radical, or a substituted or unsubstituted aromatic radical. Most preferably, each R is H or a $C_1$ to $C_3$ alkyl radical.

The cyclopentadienyl ligands of the present invention can also form neutralized compounds or salts of metals such as magnesium, thallium, potassium, lithium or sodium of the following general formula IIIb or IIIc:

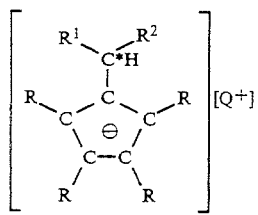

(IIIb)

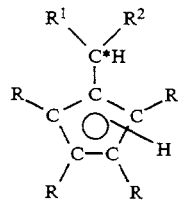

(IIIc)

wherein R, $R^1$ and $R^2$ are as defined above, and Q is selected from the group consisting of thallium, potassium, lithium, sodium, and MgX wherein X is selected from the group consisting of Cl, Br and I.

Generally the enantiomeric excess of the chiral optionally substituted cyclopentadienyl ligands of the present invention may be any desired enantiomeric excess of either the R or S enantiomer, ranging from just above the racemic mixture to even including essentially all of one enantiomer, and would depend on the desired end use of any cyclopentadienyl ligand. Such desired enantiomeric excess is generally at least about 5 percent. Preferably such enantiomeric excess is at least about 10 percent, and most preferably at least about 50 percent.

The chiral substituted cyclopentadienyl ligands of general formula III as defined above can be made by any suitable method. One such method for preparing compounds of general formula III is by contacting a substituted fulvene compound or derivative thereof of general formula I as described above with a chiral lithium salt as described above, under conditions suitable to effectuate an enantioselective hydride transfer of a hydrogen to the prochiral carbon so as to form enantiomerically enhanced cyclopentadienyl ligands of general formula III as described above. Since a chiral center is being created by the transfer of a hydride, and not merely appended to the cyclopentadienyl ligand, the reaction conditions are very critical.

The substituted fulvene compounds or derivatives thereof and the chiral lithium salt are generally contacted together in the presence of an inert atmosphere. Suitable inert atmospheres include nitrogen, argon, helium or even a vacuum.

The substituted fulvene compounds or derivatives thereof and the chiral lithium salt are generally contacted at a temperature that is sufficient to form the product cyclopentadienyl ligand of general formula III. Such temperature is generally in the range of about $-100°$ to about $+25°$ C. Preferably the temperature is in the range of about $-78°$ to about $0°$ C. Most preferably the temperature is in the range of from about $-78°$ to about $-50°$ C.

The substituted fulvene compound or derivatives thereof and the chiral lithium salt are generally contacted together at a pressure that is suitable for the formation of cyclopentadienyl ligands of general formula III. Suitable pressures include those in the range of about just above 0 psia to about 2000 psig. Preferably the pressures are in the range of from about 1 psia to about 50 psig. Most preferably the pressures are in the range of from about 0 to about 16 psig.

The substituted fulvene compound or derivative thereof and the chiral lithium salt may be contacted together in the presence of any suitable solvent that will facilitate the production of ligands of general formula III. Generally the solvent is selected from the group consisting of ethers, hydrocarbons, aromatic hydrocarbons and mixtures thereof. Preferably, the solvent selected is one in which the fulvene compound is soluble. Suitable solvents include ethers such as dimethylether, diethylether and methylethylether, hexane, toluene and benzene, and ether/hydrocarbon mixtures. Generally, when an ether/hydrocarbon mixture is used the mole ratio of ether to hyrdrocarbon is in the range of about 10:1 to about 1:10, preferably in the range of about 3:1 to about 1:3 and most preferably about 1.1:1 to about 1:1.1.

The substituted fulvene compound or derivatives thereof and the chiral lithium salt are generally contacted for a time sufficient to form cyclopentadienyl ligands of general formula III. Suitable contacting times include those in the range of from about 0.1 minutes to about 24 hours. Preferably, the contacting time is in the range of about 0.5 hours to about 16 hours. Most preferably the contacting time is in the range of 1 to about 8 hours.

The substituted fulvene compound or derivatives thereof and the chiral lithium salt are generally contacted together in mole ratios that are suitable for the formation of cyclopentadienyl ligands of general formula III. Suitable mole ratios of substituted fulvenes or derivatives thereof to lithium salt include those in the range of from about 10 to 1 to about 1 to 10. Preferably, the mole ratios are in the range of from about 3 to 1 to about 1 to 3. Most preferably the mole ratio are in the range of about 1.1 to 1 to about 1 to 1.1.

The metal containing compound suitable for use in the present invention is any compound having a transition metal that is capable of forming an organometallic complex with the chiral substituted cyclopentadienyl ligand of formula III. Typically the metal containing compound is a metal halide or metal carbonyl halide. Suitable transition metals include any Group III B through Group VIII B metal capable of forming an organometallic complex with the chiral substituted cyclopentadienyl ligand. Preferably, the transition metal is selected from Group IV B, VI B or VIII B, most preferably from Group IV B. Suitable metals include Ti, Hf, U, Th, Sc, V, Cr, Mn, Fe, Co and Zr. Preferably, the metal containing compound will contain a metal selected from the group consisting of Ti, Hf, U, Th and Zr Most preferably, the metal containing compound will contain a metal selected from the group consisting of Ti, Hf and Zr. Suitable metal containing compounds include titanium tetrachloride and zirconium tetrachloride.

The chiral organometallic complexes of the present invention can be produced by any method. A suitable method for producing the organometallic complexes of the present invention comprises contacting a chiral substituted cyclopentadienyl ligand of general formula III with a metal containing compound as described above, under suitable reaction conditions so as to form the desired chiral organometallic complex, which is typically of general formula V:

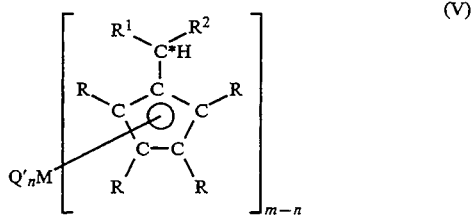

wherein R, R$^1$ and R$^2$ are as defined above, each Q' may independently be any univalent anionic ligand such as a halide, hydride, or substituted or unsubstituted C$_1$–C$_{20}$ hydrocarbyl, alkoxide, aryloxide, amide, arylamide, phosphide or arylphosphide, or both Q' together may be an alkylidene or a cyclometallated hydrocarbyl or any other divalent anionic chelating ligand, M is a transition metal as described above, m is the valence or oxidation state of the metal and n is in the range of about 1 to about m-1. Preferably, Q' is a halide selected from the group consisting of chlorine, bromine and iodine.

Generally the enantiomeric excess of the enhanced chiral organometallic complex of the present invention may be any desired enantiomeric excess of either the R or S enantiomer, ranging from just above the racemic mixture to even including essentially all of one enantiomer, and would depend on the desired end use of any catalyst produced from such organometallic complexes. Such desired enantiomeric excess is generally at least about 5 percent. Preferably such enantiomeric excess is at least about 10 percent, and most preferably at least about 50 percent.

Since the reaction of the chiral substituted cyclopentadienyl ligand of general formula III with the metal containing compound, to form the chiral organometallic complex, does not involve the breaking of a bond to the chiral center, the reaction will proceed with a retention of the configuration about that chiral center. This means that the configuration about the chiral center and the enantionmeric excess of the resulting chiral organometallic complex product will be essentially the same as the configuration about the chiral center and the enantiomeric excess of the chiral substituted cyclopentadienyl ligand from which it was derived. Therefore to obtain a chiral substituted organometallic complex product of a desired configuration and enantiomeric excess or purity, the configuration and enantiomeric excess or purity of the reactant chiral substituted cyclopentadienyl ligand will need to be substantially the same as the desired configuration and enantiomeric excess or purity.

The chiral substituted cyclopentadienyl ligand of general formula III and the metal containing compound are generally contacted at a temperature that is sufficient to form the chiral organometallic complex. Such temperature is generally in the range of about -78 to about 200° C. Preferably the temperature is in the range of about —78° to about 100° C. Most preferably the temperature is in the range of from about —78° to about 65° C.

Ligands of general formula III and the metal containing compound are generally contacted together at a pressure that is suitable for the formation of the chiral organometallic complex. Suitable pressures include those in the range of about just above 0 psia to about 2000 psig. Preferably the pressures are in the range of from about 1 psia to about 50 psig. Most preferably the pressures are in the range of from about 0 to about 16 psig.

Chiral substituted cyclopentadienyl ligands of general formula III may be contacted together with the metal containing compounds in the presence of any suitable solvent that will facilitate the production of compounds of general formula V. Generally the solvent is selected from the group consisting of ethers, glymes hydrocarbons, and aromatic hydrocarbons. Suitable solvents include ethers such as dimethylether, diethylether and methyethylether, THF, DME, Hexane, toluene, and methylene chloride.

The chiral substituted cyclopentadienyl ligands of general formula III and the metal containing compounds are generally contacted together for a time sufficient to form the desired chiral organometallic complexes. Suitable contacting times include those in the range of from about 0.1 minute to about 24 hours. Preferably, the contacting time is in the range of about 1 hour to about 16 hours. Most preferably the contacting time is in the range of 1 to about 8 hours.

The chiral substituted cyclopentadienyl ligands of general formula III and the metal containing compounds are generally contacted together in mole ratios that are suitable for the formation of compounds of desired organometallic complex. Suitable mole ratios of the chiral substituted cyclopentadienyl ligands of general formula III to the metal containing compounds include those in the range of from about 10 to 1 to about 1 to 10. Preferably, the mole ratios are in the range of from about 3 to 1 to about 1 to 3. Most preferably the mole ratios are in the range of about 1 to 1 to about 1 to 1.1.

The chiral substituted cyclopentadienyl ligands of general formula III, IIIb and IIIc are suitable as precursors for making chiral substituted organometallic complexes, which can be utilized as components in catalysts that are useful for polymerization hydrogenation, hydroformulations and epoxidation. They are very suitable as precursors for making chiral substituted organometallic complexes, which can be utilized as components in metallocene-alumoxane catalysts useful in the polymerization of polyolefins. In particular, the chiral catalyst complexes of enhanced enantiomeric purity are useful in controlling particular properties of polyolefins, including crystallinity.

The chiral organometallic complexes of the present invention are useful as the metallocene component of a supported metallocene alumoxane catalyst for use in gas phase polymerization of olefins. Supported metallocene-alumoxane catalysts and methods for making them are well known. Supported metallocene-alumoxane catalysts for olefin polymerization are described in U.S. Pat. No. 4,701,432 of Welborn. These supported metallocene-alumoxane catalysts are generally obtained by reacting a metallocene and an alumoxane in the presence of the solid support material. The supported catalyst may then be employed either as the sole catalyst component or may be employed in combination with cocatalyst.

EXAMPLES

All operations were performed under an inert atmosphere on a double manifold schlenk line or in a Vacuum Atmosphere glovebox under an atmosphere of dry nitrogen. Ether, THF and hexanes were purified by distillation from Na/K alloy undernitrogen. Dichloromethane was distilled from $P_2O_5$ (Fisher) prior to use. Methanol (Aldrich), pyrrolidine (Aldrich), acetic acid (Fisher), magnesium sulfate (Fisher), sodium bicarbonate (Fisher), hydrochloric acid (Fisher), acetone (Aldrich), isobutyraldehyde (Aldrich), benzaldehyde (Aldrich), 2-butanone (Aldrich), trimethylacetaldehyde (Aldrich), acetophenone (Aldrich), n-butyllithium (Aldrich), 1,2,3,4-tetrahydroisoquinoline (Aldrich), l-proline (Aldrich), (s)-(−)-pyrrolidone-5-carboxylic acid (Aldrich), dicyclopentadiene (Aldrich), methyllithium (Aldrich), sodium hydride (Aldrich), potassium hydride (Aldrich), methylmagnesium bromide (Aldrich), isopropylmagnesium chloride (Aldrich), ferrous chloride (Srrem), cyclopentadienyltitanium trichloride(Strem), zirconium tetrachloride (Alfa) and fluorene (Fluka) were used as purchased. Diethylamine (Aldrich) was distilled from BaO (Aldrich) prior to use.

$^1$H NMR spectra were reduced at 250 MHz on a Bruker 250 MHz NMR spectrometer. Spectra were measured at ambient temperatures in $CDCl_3$, using tetramethylsilane as an internal standard. GC/MS were recorded on a Hewlett-Packard 5995 Gas Chromatography/Mass Spectrometer using a HP-1 crosslinked methyl silicone gum column (12 m×0.2 mm×0.33 μm film thickness).

Example 1

Preparation of 6-methyl-6-phenylfulvene

To a solution of 28 mL of acetophenone (0.24 mol) and 20 mL of freshly cracked cyclopentadiene (0.24 mol) in 100 ml of methanol was added 30 mL of pyrrolidine (0.36 mol). The resulting solution was stirred overnight at room temperature. Acetic acid, 21 mL, (0.37 mol) was added to the solution. The solvent was removed under vacuum and the residue diluted with 40 mL each of ether and water. The aqueous layer was extracted with two 30 mL portion of ether and the combined organic layers were washed with 40 mL of water, and then dried over $MgSO_4$. Removal of solvent gave a deep red oil. This deep red oil was purified by column chromatography using hexane as the eluant. The packing material was silica gel. Removal of solvent gave 20 g (50% yield) of 6-methyl-6-phenylfulvene[21] as a deep red oil.

$^1$H NMR (250 MHz, $CDCl_3$); δ: 7.35–7.29 (m, 5H); 6.62–6.60 (m, 1H); 6.55 (m, 1H); 6.46–6.44 (m, 1H); 6.19–6.17 (m, 1H); 2.48 (s, 3H).

Example 2

Li salt of L-proline + 6-methyyl-6-phenylfulvene n-BuLi (15 mL, 1.6M in hexanes, 24 mmol) was added dropwise to 1.4 g (12 mmol) of L-proline in 40 mL of ether. The resulting suspension was allowed to stir at room temperature over night. The reaction mixture was cooled to −78° C. and 2.0 g (12 mmol) of 6-methyl-6-phenylfulvene added dropwise. The reaction mixture was stirred at −78° C. for eight hours. The reaction mixture was allowed to warm to room temperature and the organic and aqueous layers were separated. The organic layer was dried over $MgSO_4$ and the solvent removed under vacuum to give 2.05 g (100% yield) of (1-phenylethyl)cyclopentadiene as a yellow oil. The product was found to have a specific rotation of 4°(12% ee).

Example 3

Reduction of 6-methyl-6-phenylfulvene with dilithio-l-proline in ether/hexane (3:1)

To a solution of 1.4 g. of l-proline (12 mmol) in 40 mL of ether was added 15 mL of n-BuLi (1.6M solution in hexanes, 24 mmol) at 0° C. This solution was stirred overnight at room temperature and then cooled to −78° C. 6-Methyl-6-phenylfulvene, 2.0 g, (12 mmol) in 5 mL of ether was added dropwise at −78° C. The resulting solution was stirred 6 h at −78° C. Water, 20 mL, was added dropwise at −78° C. and the solution warmed to room temperature. The organic layer was separated and washed with aqueous $NaHCO_3$, $H_2O$ and then dried over $MgSO_4$. Removal of the solvent gave 2.0 g (99% yield) of 1-cyclopentadienyl-1-phenylethane as a light yellow oil. $_D$=3.0° ($CHCl_3$), 8.7% ee.

Example 4

Reduction of 6-methyl-6-phenylfulvene with dilithio-l-proline in THF n-BuLi, 15 mL, (1.6M solution in hexanes, 24 mmol) was added to a 100 mL three necked round bottom flask with nitrogen inlet. The solvent was removed under vacuum. THF, 30 mL, was added and 1.4 g of l-proline (12 mmol) in 10 mL of THF was added dropwise at 0° C. This solution was stirred overnight at room temperature. 6-Methyl-6-phenylfulvene, 2.0 g, (12 mmol) was added dropwise at −78° C. The resulting solution was stirred for 5 h at −78° C., 5 h at 0° C., and overnight at room temperature. Water, 20 mL, was added at 0° C. and the solution warmed to room temperature. The organic layer was separated and washed with aqueous $NaHCO_3$, $H_2O$ then dried over $MgSO_4$. Removal of solvent gave 1.2 g (60%) recovery of unreacted 6-methyl-6-phenylfulve.

Example 5

Reduction of 6-methyl-6-phenylfulvene with dilithio (S)-(−)-2-pyrrolidone-5-carboxylic acid in ether/hexanes (5.8:1)

To a solution of 0.77 g of dilithio (s)-(−)-2-pyrrolidone-5-carboxylic acid (6 mmol) in 40 mL of ether was added 7.8 mL of n-BuLi (1.6M solution in hexances, 13 mmol) at 0° C. This solution was stirred for 30 min at room temperature. 6-Methyl-6-phenylfulvene, 1.0 g, (6 mmol) in 5 mL of ether was added dropwise at −78° C. and the color of the reaction mixture turned green. The resulting solution was stirred for 7 h at −78° C. and the solution warmed to room temperature. The organic layer was separated and washed with aqueous NaHCO$_3$, H$_2$O and then dried over MgSO$_4$. Removal of solvent gave 1.0 g (99% yield) of 1-cyclopentadienyl-1-phenyl-ethane as a light yellow oil. $[\alpha]_D = 6.0°$ (CHCl$_3$), 17.4% ee.

Example 6

Reduction of 6-methyl-6-phenylfulvene with dilithio (S)-(−)-2-pyrrolidone-5-carboxylic acid in ether/hexanes (2.8:1)

To a solution of 1.5 g of dilithio (s)-(−)-2-pyrrolidone-5-carboxylic acid (12 mmol) in 40 mL of ether was added 16 mL of n-BuLi (1.6M solution in hexanes, 25 mmol) at 0° C. This solution was stirred for 30 min at room temperature. 6-Methyl-6-phenylfulvene, 1.0 g,(6 mmol) in 5 mL of ether was added dropwise at −78° C. and the color of the reaction mixture turned green. The resulting solution was stirred for 7 h at −78° C. and the color of the reaction mixture turned yellow. Water, 25 mL, was added dropwise at −78° C. and the solution warmed to room temperature. The organic layer was separated and washed with aqueous NaHCO$_3$, H$_2$O and then dried over MgSO$_4$. Removal of solvent gave 1.0 g (99% yield) of 1-cyclopentadienyl-1-phenylethane as a light yellow oil. $[\alpha]_D = 6.0°$ (CHCl$_3$, 17.4% ee.

Example 7

Reduction of 6-methyl-6-phenylfulvene with dilithio (s)-(−)-2-pyrrolidone-5-carboxylic acid in ether To a solution of 0.77 g of dilithio (s)-(−)-2-pyrrolidone-5-carboxylic acid (6 mmol) in 40 mL of ether was added 7.8 mL of n-BuLi (1.6 m solution in hexanes, 13 mmol) at 0° C. This solution was stirred for 30 min at room temperature. The solvent was removed under vacuum and 25 mL of ether added. 6-Methyl-6-phenylfulvene, 1.0 g, (6 mmol) in 5 mL of ether was added dropwise at −78° C. and the color of the reaction mixture turned green. The resulting solution was stirred for 7 h at −78° C. and the color of the reaction mixture turned yellow. Water, 25 mL, was added dropwise at −78° C. and the solution warmed to room temperature. The organic layer was separated and washed with aqueous NaHCO$_3$, H$_2$O and then dried over MgSO$_4$. Removal of solvent gave 0.9 g (89% yield) of 1-cyclopentadienyl-1-phenylethane as a light yellow oil. $[\alpha]_D = 2.0°$ (CHCL$_3$), 5.8% ee.

Example 8

Reduction of 6-methyl-6-phenylfulvene with dilithio (s)-(−)-2-pyrrolidone-5-carboxylic acid in hexane To a solution of 0.77 mL of dilithio (s)-(−)-2-pyrrolidone-5-carboxylic acid (6 mmol) in 40 mL of ether was added 7.8 mL of n-BuLi (1.6M solution in hexanes, 13 mmol) at 0° C. This solution was stirred for 30 min at room temperature. The solvent was removed under vacuum and 25 mL of hexane added. 6-Methyl-6-phenylfulvene, 1.06 (6 mmol) in 5 mL of hexane was added dropwise at −78° C. The resulting yellow solution was stirred for 7 h at −78° C. Water, 25 mL, was added dropwise at −78° C. and the solution warmed to room temperature. The organic layer was separated and washed with aqueous NaHCO$_3$, H$_2$O and then dried over MgSO$_4$. Removal of solvent gave 0.8 g (79% yield) of 1-cyclopentadienyl-1-phenylethane as a light yellow oil. $[\alpha]_D = 2.0°$ (CHCl$_3$), 5.8% ee.

Example 9

Reduction of 6-methy-6-phenylfulvene with dilithio (s)-(−)-2-pyrrolidone-5-carboxylic acid in ether/hexane (5.1:1) at room temperature To a solution of 0.77 mL of dilithio (s)-(−)-2-pyrrolidone-5-carboxylic acid (6 mmol) in 40 mL of ether was added 7.8 mL of n-BuLi (1.6M solution in hexanes, 13 mmol) at 0° C. This solution was stirred for 30 min at room temperature. 6-Methyl-6phenylfulvene, 1.0 g, (6 mmol) was added dropwise at 0° C. and the solution warmed to room temperature. The organic layer was separated and washed with aqueous NaHCO$_3$, H$_2$O and then dried over MgSO$_4$. Removal of solvent gave 1.0 g (99% yield) of 1-cyclopentadienyl-1-phenylethane as a light yellow oil. $[\alpha]_D = 0.0°$ (CHCl$_3$).

Example 10

Preparation of [C$_5$H$_5$][C$_5$H$_4$(CH(CH$_3$)C$_6$H$_5$]Fe

To a solution of 0.6 g of 1-cyclopentadienyl-1phenylethane (3.5 mmol) ($[\alpha]_D = 3$, 8.7% ee) in 15 mL of THF was added 2.2 mL of n-BuLi (1.6M solution in hexanes, 3.5 mmol) at 0° C. This solution was stirred for 2 h at room temperature. To a solution of 0.29 mL of cyclopentadiene (3.5 mmol) in 15 mL of THF was added 2.2 mL of n-BuLi (1.6M solution in hexanes, 3.5 mmol) at 0° C. This solution was stirred for 2 h at room temperature. These two solutions were combined and 0.45 g of anhydrous ferrous chloride (3.5 mmol) was added at 0° C. The mixture was refluxed for 2 h, during which the solution turned dark red. The solution was then cooled to room temperature and the solvent removed under vacuum. The residue was taken up in ether and washed with saturated aqueous ammonium chloride. The organic layer was separated, dried over MgSO$_4$ and then filtered. Removal of the solvent gave 0.9 g yellow solid. This yellow solid was purified by silica gel column chromatography using hexane as the eluent. Removal of the solvent gave 0.3 of [C$_5$H$_5$][C$_5$H$_4$(CH(CH$_3$)C$_6$H$_5$)]Fe as a yellow oil. $[\alpha]_D = 11.54°$ (hexane), 10.5% ee.

Example 11

Preparation of [C$_5$H$_5$][C$_5$H$_4$(CH(CH$_3$)C$_6$H$_5$)TiCl$_2$

To a solution of 0.7 g of 1-cyclopentadienyl-1phenylethane (17.4% ee) 4.1 mmol) in 15 mL of ether was added 2.7 mL of n-BuLi (1.6M solution in hexanes, 4.3 mmol at 0° C. This solution was stirred for 2 h at room temperature. The reaction mixture was cooled to 0° C. and cyclopentadienyltitanium trichloride, 0.90 g, (4.1 mmol) was added at 0° C. The resulting solution was allowed to warm to room temperature and refluxed for 3 h. The solvent was removed under vacuum and the solid taken up in 20 mL of dichloromethane. The resulting suspension was then filtered and the solvent removed under vacuum to give 0.7 g (48% yield) of [C$_5$H$_5$][C$_5$H$_4$(CH(CH$_3$)C$_6$H$_5$)]TiCl$_2$ as a red solid.

The invention has been described with reference to its preferred embodiments. Those of ordinary skill in the art may, upon reading this disclosure, appreciate changes or modifications which do not depart from the scope and spirit or the invention as described above or claimed hereafter.

Example 12

Preparation of [C$_5$H$_4$(CH(CH$_3$)C$_6$H$_5$)]$_2$ZrCl$_2$

To a solution of 0.7 g of 1-cyclopentadienyl-1-phenylethane (17.4% ee) (4.1 mmol) in 15 mL of ether was added 2.7 mL of n-BuLi (1.6M solution in hexanes, 4.3 mmol) at 0° C. This solution was stirred for 2 h at room temperature. The reaction mixture was cooled to 0° C. and zirconium tetrachloride, 0.24 g, (2.1 mmol) was added. The resulting solution was allowed to warm to room temperature and refluxed for 3 h. The solvent was removed under vacuum and the solid taken up in 20 mL of dichloromethane. The resulting suspension was then filtered and solvent removed under vacuum to give 0.8 g (78% yield) of [C$_5$H$_4$(CH(CH$_3$)C$_6$H$_5$)]$_2$ZrCl$_2$ as a pale yellow solid.

What is claimed

1. A method of making enantiomerically enhanced chiral optionally substituted cyclopentadienyl ligand represented by the general formula III:

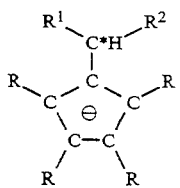

comprising contacting an optionally substituted fulvene having a prochiral carbon at the carbon 6 position represented by the general formula 1:

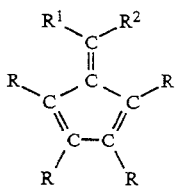

with a lithium salt under suitable reaction conditions so as to form the enantiomerically enhanced cyciopentadienyl ligand of general formula III, wherein C* is a chiral carbon center: each R is independently selected from the group consisting of H or C$_{1-12}$ substituted aliphatic, unsubstituted aliphatic, substituted cyclic, unsubstituted cyclic, substituted heterocyclic, and unsubstituted heterocyclic radicals or two neighboring R groups are joined to provide a ring of five or more carbon atoms; R$^1$ and R$^2$ are not the same and are each independently selected from the group consisting of H or a C$_{1-8}$ substituted aliphatic, unsubstituted aliphatic, substituted cyclic, unsubstituted cyclic, substituted heterocyclic, and unsubstituted heterocyclic radicals; and the lithium salt is a lithium salt of at least one selected from the group consisting of chiral amines, chiral amides, and chiral amino acids, all of which have a hydrogen on a carbon alpha to the nitrogen, wherein the chiral amines are selected from the group or chiral primary and secondary cyclic, acyclic, heterocyclic, open chain and functionalized amines, and the chiral amide are selected from the group consisting of chiral cyclic, acyclic, and heterocyclic amides.

2. The method of claim 1 wherein the fulvene and the lithium salt are contacted together at a temperature in the range of about −100° C. to about 25° C., at a pressure in the range of about just above 0 psia to about 200 psig, for a contacting time in the range of about 0.1 minute to about 24 hours, and at a mole ratio of fulvene to lithium salt in the range of about 10 to 1 to about 1 to 10.

3. The method of claim 2 wherein the chiral cyclopentadienyl ligands of general formula III are produced at an enantionmeric excess of at least 5 percent.

4. The method of claim 1 wherein each R is independently selected from the group consisting of H and alkyl, substituted aromatic and unsubstituted aromatic radicals or two R groups are joined to provide a ring of 5 or more carbon atoms; R$^1$ and R$^2$ are not the same and each is independently selected from the group consisting of alkyl, substituted aromatic and unsubstituted aromatic radicals, and the amine is a chiral secondary amine.

5. The method of claim 4 wherein the fulvene and the lithium salt are contacted together at a temperature in the range of about −78° C. to about 0° C., at a pressure in the range of about 1 psia to about 50 psig, for a contacting time in the range of about 0.5 to about 16 hours, and at a mole ratio of fulvene to lithium salt in the range of about 3 to 1 to about 1 to 3.

6. The method of claim 5 wherein the fulvene is a 6-alkyl-6-arylfulvene..

7. The method of claim 6 wherein the lithium salt is selected from the group consisting of lithium salt of 2-methylindoline, dilithium salt of (S)-(−)-2-pyrrolidone-5-carboxylic acid and dilithium salt of L proline.

8. The method of claim 5 wherein the chiral cyclopentadienyl ligands of general formula III are produced at an enantionmeric excess of at least 10 percent.

9. The method of claim 1 wherein the chiral cyclopentadienyl ligands of general formula III are produced at an enantionmeric excess of at least 5 percent.

10. The method of claim 9 wherein each R is independently selected from the group consisting of H, methyl, ethyl and propyl.

11. The method of claim 10 wherein the fulvene and the lithium salt are contacted together at a temperature in the range of about −78° to about −50° C., at a pressure in the range of about 0 to about 16 psig, for a contacting time in the range of about 1 to about 8 hours, and at a mole ratio of fulvene to lithium salt in the range of about 1.1 to 1 to about 1 to 1.1.

12. The method of claim 11 wherein the fulvene is selected from the group consisting of 6-methyl-6-phenylfulvene, 6-methyl-6-ethylfulvene, 6-methyl-6-propylfulvene, 6-ethyl-6-propyl-fulvene, 6-ethyl-6-phenylfulvene, and 6-propyl-6-phenylfulvene.

13. The method of claim 1 wherein the substituted fulvene and the lithium salt are contacted together in the presence of a solvent selected from the group consisting of ethers, hydrocarbons, aromatic hydrocarbons and mixtures thereof.

14. The method of claim 13 wherein the lithium salt is selected from the group consisting of the lithium salt of 2-methylindoline, the dilithium salt of (S)-(—)-2-pyrrolidone-5-carboxylic acid and the dilithium salt of L proline.

15. A method of making enantionmerically enhanced chiral optionally substituted cyclopentadienyl ligands of general formula III:

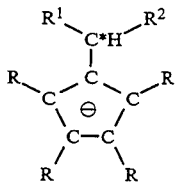

comprising contacting an optionally substituted fulvene having a prochiral carbon at the carbon 6 position of general formula I:

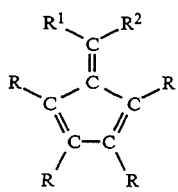

with a lithium salt under suitable reaction conditions so as to form the enantiomerically enhanced cyclopentadienyl ligand of general formula III at an enantiomeric excess of at least 5 percent; wherein C* is a chiral carbon center; each R is independently selected from the group consisting of H or a $C_{1-12}$ substituted aliphatic, unsubstituted aliphatic, substituted cyclic, unsubstituted cyclic, substituted heterocyclic, and unsubstituted heterocyclic radicals or two neighboring R groups are joined to provide a ring of five or more carbon atoms or each R is independently selected from the group consisting of H, methyl, ethyl, and propyl $R^1$ and $R^2$ are not the same and are each independently selected from the group consisting of H or a $C_{1-8}$ substituted aliphatic, unsubstituted aliphatic, substituted cyclic, unsubstituted cyclic, substituted heterocyclic, and unsubstituted heterocyclic radicals: and the lithium salt is a lithium salt of at least one selected from the group consisting of chiral amines, chiral amides, and chiral amino acids, all of which have a hydrogen on a carbon alpha to the nitrogen, wherein the chiral amines are selected from the group consisting of chiral primary and second acyclic, acyclic, heterocyclic, open chain and functionalized amines, and the chiral amides are selected from the group consisting of chiral cyclic, acyclic, and heterocyclic amides;

the fulvene and the lithium salt are contacted together at a temperature in the range of about —78° to —50° C., at a pressure in the range of about 0 to about 16 psig, for a contacting time in the range of about 1 to about 8 hours, and at a mole ratio of fulvene to lithium salt in the range of about 1.1 to 1 to about 1 to 1;

the fulvene is selected from the group consisting of 6-methyl-6-phenylfulvene, 6-methyl-6-ethylfulvene, 6-methyl-6-propylfulvene, 6-ethyl-6-propylfulvene, 6-ethyl-6-phenyifulvene, and 6proyl-6-phenylfulvene;

the substituted fulvene and the lithium salt are contacted together in the presence of a solvent selected from the group consisting of ethers, hydrocarbons, aromatic hydrocarbons and mixtures thereof; and the lithium salt is selected from the group consisting of the lithium salt of 2-methylindoline, the dilithium salt of(s)-(—)-2-pyrrolidone-5-carboxylic acid and the dilithium salt of L proline.

16. An enantiomerically enhanced composition comprising at least an enantiomeric excess of 5 percent, said enantiomerically enhanced composition comprising chiral optionally substituted cyclopentadienyl compounds of the general formula IIIb:

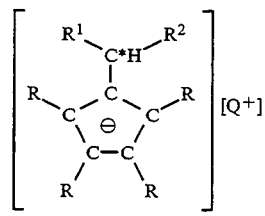

wherein C* is a chiral carbon center; each R is independently selected from the group consisting of H, or a $C_{1-12}$ alkyl, substituted aliphatic, unsubstituted aliphatic, substituted cyclic, unsubstituted cyclic, substituted heterocyclic, and unsubstituted heterocyclic radicals or two neighboring R groups are joined to provide a ring of 5 or more carbon atoms; $R^1$ and $R^2$ are not be the same and each is independently selected from the group consisting of alkyl. aryl, phenyl, H or a $C_{1-8}$ substituted aliphatic, unsubstituted aliphatic, substituted aromatic, unsubstituted aromatic, substituted cyclic, unsubstituted cyclic, substituted heterocyclic and unsubstituted heterocyclic radicals, and Q is selected from the group consisting of thallium, potassium, lithium, sodium, and MgX wherein X is selected from the group consisting of Cl, Br, and I.

17. An enantiomerically enhanced composition, comprising an enantiomeric excess of at least 5 percent, said enantiomerically enhanced composition having chiral optionally substituted cyclopentadienyl compounds of the general formula IIIc:

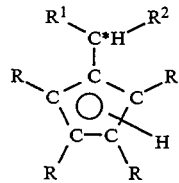

wherein C* is a chiral carbon center; each R is independently selected from the group consisting of H, alkyl, $C_{1-12}$ substituted aliphalic, unsubstituted aliphatic, unsubstituted aromatic, substituted aromatic, substituted cyclic, unsubstituted cyclic, substituted heterocyclic, and unsubstituted heterocyclic radicals or two neighboring R groups are joined to provide a ring of 5 or more carbon atoms; $R^1$ and $R^2$ are not be the same and each is independently selected from the group consisting of alkyl, aryl, phenyl, $C_{1-8}$ substituted aliphatic, unsubstituted aliphatic, substituted aromatic, unsubstituted aromatic, substituted cyclic, unsubstituted cyclic, substituted heterocyclic, and unsubstituted heterocyclic radicals.

* * * * *